United States Patent

Ferland et al.

Patent Number: 5,948,935
Date of Patent: Sep. 7, 1999

[54] PROCESS AND INTERMEDIATES FOR (S)-α-AMINO-1-CARBOXYCYCLOPENTANEACETIC ACID

[75] Inventors: Jean-Marie Ferland, St-Laurent; Ingrid Guse, Kirkland; Eric Malenfant, Rosemere, all of Canada

[73] Assignee: Boehringer Ingelheim (Canada) Ltd., Laval, Canada

[21] Appl. No.: 09/012,237

[22] Filed: Jan. 23, 1998

Related U.S. Application Data

[60] Provisional application No. 60/035,988, Jan. 23, 1997.

[51] Int. Cl.$^6$ .................... C07C 69/74; C07C 61/06
[52] U.S. Cl. .................... 560/122; 562/504; 558/432
[58] Field of Search .................... 560/122; 562/504; 558/432

[56] References Cited

U.S. PATENT DOCUMENTS

| | | | |
|---|---|---|---|
| 4,795,740 | 1/1989 | Cohen et al. | 514/14 |
| 4,814,432 | 3/1989 | Freidinger et al. | 530/329 |
| 5,856,518 | 1/1999 | Akiba et al. | |

FOREIGN PATENT DOCUMENTS

| | | |
|---|---|---|
| 0 411 334 A1 | 2/1991 | European Pat. Off. . |
| 0 412 595 A1 | 2/1991 | European Pat. Off. . |
| 0 560 267 A1 | 9/1993 | European Pat. Off. . |
| 0 618 226 A1 | 10/1994 | European Pat. Off. . |
| 96/37470 | 11/1996 | WIPO . |

OTHER PUBLICATIONS

Moss et al., An Enatioselective . . . Scale, Synthesis–J. of Synthetic Org. Chem., No. 1, pp. 32–34, Jan. 1997.

Chang, L.L. et al., "Substituted Penta–and Hexapeptides as Potent Inhibitors of Herpes Simplex Virus Type 2 Ribonucleotide Reductase," *Bioorganic Med. Chem. Lett.* 2(10):1207–1212 (1992).

Gaudreau, P. et al., "Synthesis and Inhibitory Potency of Peptides Corresponding to the Subunit 2 C–Terminal Region of Herpes Virus Ribonucleotide Reductase," *J. Med. Chem.* 33(2):723–730 (1990).

Liuzzi, M. et al., "A potent peptidomimetic inhibitor of HSV ribonucleotide reductase with antiviral activity in vivo," *Nature* 372:695–698 (1994).

Moss, N. et al., "Peptidomimetic Inhibitors of Herpes Simplex Virus Ribonucletide Reductase with Improved in Vivo Antiviral Activity," *J. Med. Chem.* 39(21):4173–4180 (Oct. 1996).

Moss, N. et al., "Inhibition of Herpes Simplex Virus Type 1 Ribonucleotide Reductase by Substituted Tetrapeptide Derivatives," *J. Med. Chem.* 36(20):3005–3009 (1993).

Moss, N. et al., "Herpes Simplex Virus Ribonucleotide Reductase Subunit Association Inhibitors: the Effect and Conformation of β–Alkylated Aspartic Acid Derivatives," *Bioorganic Med. Chem.* 2(9):959–970 (1994).

Moss, N. et al., "Peptodomimetic Inhibitors of Herpes Simplex Virus Ribonucleotide Reductase: A New Class of Antiviral Agents," *J. Med. Chem.* 38(18):3617–3623 (1995).

*Primary Examiner*—Samuel Barts
*Assistant Examiner*—Rosalynd Keys
*Attorney, Agent, or Firm*—Robert P. Raymond; Anthony P. Bottino; Alan R. Stempel

[57] ABSTRACT

Disclosed herein is a process for preparing (S)-α-amino-1-carboxycyclopentaneacetic acid which is a useful intermediate for preparing peptidomimetic inhibitors of herpes viral ribonucleotide reductase. The process comprises the preparation of the key intermediate

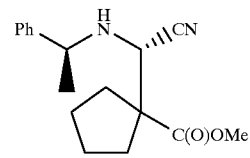

and its subsequent conversion to the desired product.

7 Claims, No Drawings

PROCESS AND INTERMEDIATES FOR (S)-α-AMINO-1-CARBOXYCYCLOPENTANEACETIC ACID

This application claims the benefit of the filing date of provisional application 60/035,988 filed on Jan. 23, 1997, which is herein incorporated by reference.

FIELD OF THE INVENTION

This invention relates to processes for preparing amino acid and peptide derivatives. The amino acid and peptide derivatives are useful intermediates in the synthesis of herpesvirus ribonucleotide reductase inhibiting compounds.

BACKGROUND OF THE INVENTION

Herpes viruses inflict a wide range of diseases against humans and animals. For instance, herpes simplex viruses, types 1 and 2 (HSV-1 and HSV-2), are responsible for cold sores and genital lesions, respectively; varicella zoster virus (VZV) causes chicken pox and shingles; and the Epstein-Barr virus (EBV) causes infectious mononucleosis.

Inhibitors of herpesvirus ribonucleotide reductase have been found to exhibit antiherpes activity. Indeed, several reports of peptide derivatives having inhibitory activity against the herpesvirus ribonucleotide reductase enzyme have been reported. For example, see the following references:

- E. A. Cohen et al., U.S. Pat. No. 4,795,740, Jan. 3, 1989,
- R. Freidinger et al., U.S. Pat. 4,814,432, Mar. 21, 1989,
- P. Gaudreau et al., *J. Med. Chem.* 1990, 33, 723,
- J. Adams et al., European patent application 411,334, published Feb. 6, 1991,
- R. L. Tolman et al., European patent application 412, 595, published Feb. 13, 1991,
- L. L. Chang et al., *Bioorg. Med. Chem. Lett.* 1992, 2, 1702,
- P. L. Beaulieu et al., European patent application 560 267, published Sep. 15, 1993,
- N. Moss et al., *J. Med.Chem.* 1993, 36, 3005,
- R. Déziel and N. Moss, European patent application 618 226, published Oct. 5, 1994,
- N. Moss et al., *Bioorg. Med. Chem.* 1994, 2, 959,
- M. Liuzzi et al., *Nature* 1994, 372, 695,
- N. Moss et al., *J. Med. Chem.* 1995, 38, 3617, and N. Moss et al., J. Med. Chem. 1996, 39, 4173.

It has recently been demonstrated that replacement of an aspartic acid residue with an (S)-α-amino-1-carboxycyclopentaneacetic acid residue in this type of inhibitor improved potency 50-fold (N. Moss, et al., *Bioorg. Med. Chem.* 1994, 2, 959). Apparently, the cyclopentyl group improved inhibitor potency by strongly favoring a specific conformation, namely the S configuration of the aspartic acid side chain, that facilitated binding the enzyme. This modification also proved vital in obtaining inhibitors with good antiviral activity in vitro and in vivo (M. Liuzzi et al., Nature 1994, 372, 695; N. Moss et al., *J. Med. Chem.* 1995, 38, 3617). The critical importance of the (S)-α-amino-1-carboxycyclopentaneacetic acid moiety makes a facile enantioselective synthesis of this amino acid derivative highly desirable.

N. Moss et al., *J. Med. Chem.* 1995, 38, 3617 disclose a procedure for the synthesis of a precursor of (S)-α-amino-1-carboxycyclopentaneacetic acid. This derivative could readily be incorporated into peptide and peptidomimetic inhibitors. However the synthesis of this precursor requires carefully controlled low temperature conditions (−78° C.) and purification by chromatography. These requirements can be impractical for the large scale preparation of this compound.

To circumvent these problems, a synthesis that would avoid low temperature reactions and difficult purifications is required. Therefore, efficient and low cost methods which are amenable to scale-up are needed for the preparation of (S)-α-amino-1-carboxycyclopentaneacetic acid.

The process disclosed herein fulfills these needs.

The present process, and key intermediate compounds prepared by the present process, can be distinguished readily from the prior art. The intermediate compounds of the process possess novel chemical structures.

SUMMARY OF THE INVENTION

Disclosed herein is a process for preparing (S)-α-amino-1-carboxycyclopentaneacetic acid which comprises the following steps:

(i) reacting methyl 1-formylcyclopentanecarboxylate with the chiral amine auxiliary (S)-α-methylbenzylamine to obtain the corresponding Schiff base, (ii) reacting the Schiff base with a cyanide source in the presence of a Lewis acid to obtain a mixture of the α-amino nitriles of formulae 1 and 2

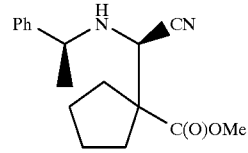

(1)

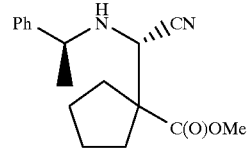

(2)

in a R:S ratio of at least 1:15–30, (iii) subjecting the latter mixture to selective acid hydrolysis to obtain predominantly the amino amide 3

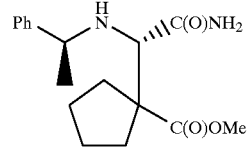

(3)

(iv) subjecting the amino amide 3 to hydrogenolysis in the presence of aqueous HCl to obtain the corresponding N-terminal derivative 4

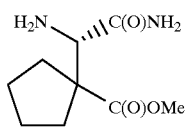

followed by hydrolysis of the latter compound with excess 6 N aqueous HCl to obtain the hydrochloride salt of (S)-α-amino-1-carboxycyclopentaneacetic acid; and (v) reacting the hydrochloride salt with a base capable of transforming the hydrochloride salt to (S)-α-amino-1-carboxycyclopentaneacetic acid.

In a preferred process the mixture of the α-amino nitriles of formulae 1 and 2, obtained according to step (ii), is crystalized from or triturated in hexane to give essentially, enantiomerically pure α-amino nitrile 2, which in turn is subjected serially to steps iii, iv and v to give (S)-α-amino-1-carboxycyclopentaneacetic acid.

Preferred cyanide sources for the preceding process include trimethylsilyl cyanide, acetone cyanohydrin, diethylaluminum cyanide and potassium cyanide.

Preferred Lewis acids for the proceding processes include $TiCl_4$, $SnCl_4$, $ZnCl_2$, trimethylsilyl trifluoromethanesulfonate, $Me_3Al$, $Et_2AlCl$ and $EtAlCl_2$.

DETAILED DESCRIPTION OF THE INVENTION

General (S)-α-amino-1-carboxycuclopentaneacetic acid can be represented by the following formula

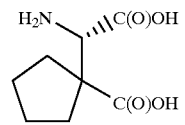

With reference to the instances where (R) or (S) is used to designate the configuration of a radical, the designation is done in the context of the compound and not in the context of the radical alone.

The term "residue" with reference to an amino acid or amino acid derivative means a radical derived from the corresponding α-amino acid by eliminating the hydroxyl of the carboxy group and one hydrogen of the α-amino group.

Process

More explicitly, the present process involves reacting methyl 1-formylcyclopentanecarboxylate with (S)-α-methylbenzylamine (Aldrich Chemical Company, Inc., Milwaukee, Wis., USA) to give the corresponding Schiff base under standard conditions. Next, the Schiff base is reacted with a cyanide source (for example, trimethylsilyl cyanide, acetone cyanohydrin, diethylaluminum cyanide or KCN) in the presence of a Lewis acid (for example, $TiCl_4$, $SnCl_4$, $ZnCl_2$, trimethylsilyl trifluoromethanesulfonate (Aldrich Chemical Company), $Me_3Al$, $Et_2AlCl$, $EtAlCl_2$), in an organic solvent (for example, tetrahydrofuran, dichloromethane, toluene, or hexane) to give a mixture of the corresponding α-amino nitriles 1 and 2. Under these conditions, amino nitriles 1 and 2 could be reproducibly obtained in an R:S ratio of 1:15–30 with a combined yield up to 95% (0.4 mole scale). This degree of diastereoselectivity is especially noteworthy for this type of reaction.

The mixture of amino nitriles 1 and 2 can then be transformed by the aforementioned steps iii, iv, v to give predominantly (S)-α-amino-1-carboxycyclopentane acetic acid. Thereafter, and if desired, the latter compound can be reacted with di-tert-butyl dicarbonate to provide the corresponding N-tert-butyloxycarbonyl (N-Boc) derivative in sufficient purity for use in preparing herpesvirus ribonucleotide reductase inhibitors according to known methods; for example, see N. Moss et al., *J. Med. Chem.* 1995, 38, 3617.

The procedures described hereinbefore can be modified when the molar amounts of the starting materials and subsequent reactants are increased >5.7 mole. Under these conditions, it was found that α-amino nitriles 1 and 2 were obtained in a more modest 1:4.5 ratio. However, α-amino nitrile 2 can readily be separated from the undesired isomeric α-amino nitrile 1 by one crystallization/precipitation from hexane (62% yield of pure 2).

Moreover, the concentrated mother liquors, which contain a higher proportion of isomeric α-amino nitrile 1 can be readily equilibrated to a 1:4–5 ratio mixture of the α-amino nitriles of formulae 1 and 2, by stirring the mother liquid with potassium carbonate and methanol. Crystallization of the equilibrated product provides an additional quantity of pure α-amino nitrile 2, typically 50% of the concentrated mother liquors.

The following examples illustrate further this invention. Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Abbreviations used in the specification include Boc: tert-butyloxycarbonyl; DMF: dimethylformamide; EtOAc: ethyl acetate; $Et_2O$: diethyl ether, HPLC: high performance liquid chromatography; Me: methyl; MeOH: methanol; Ph:phenyl; TLC: thin layer chromatography.

EXAMPLE 1

Methyl 1-Cyanocyclopentanecarboxylate

To a 22 L flask equipped with a mechanical stirrer, thermometer and condenser containing a nitrogen inlet was added dry DMF (8 L) and methyl cyanoacetate (800 g, 8.07 mol). Stirring was started and $K_2CO_3$ (2.67 kg, 19.3 mol) and then 1,4-dibromobutane (1.74 kg, 8.07 mmol) were added. The exothermic reaction mixture (temperature increased to 75° C.) was stirred at room temperature for 16 h followed by heating at 60–75° C. for 3 h. Approximately 2.5 L of solvent were removed under reduced pressure and the residue was diluted with water (8 L). The resultant mixture was extracted with $Et_2O$ (2×2 L) and the combined organic phases were washed with 1 N aqueous HCl and brine. Drying ($MgSO_4$), filtering and concentrating afforded an orange liquid. This material was distilled (fraction boiling at 80° C., 0.7 mm Hg collected) to provide methyl 1-cyanocyclopentanecarboxylate as a clear colorless liquid (953 g, 77% yield). $^1$H-NMR (400 MHz, $CDCl_3$) δ 3.80 (s, 3 H), 2.29-2.22 (m, 4 H), 1.90-1.84 (m, 4 H); $^{13}$C NMR (100.6 MHz, $CDCl_3$) δ 169.2, 119.9, 52.6, 46.6, 36.9, 24.3; EI-MS exact mass calcd for $C_8H_{11}NO_2$: 153.0790; found: 153.0785.

EXAMPLE 2

Methyl 1-Formylcyclopentanecarboxylate

To a 12 L flask equipped with a mechanical stirrer, thermometer and condenser containing a nitrogen inlet was added Raney nickel (1 kg, 50% slurry in water, as sold by the Aldrich Chemical Co.). This material was washed with distilled water and decanted (3×0.8 L). Formic acid (88% 7 L) was added (stirring started) followed by a solution of methyl 1-cyanocyclopentanecarboxylate (696 g, 4.54 mol) in formic acid (88%, 1 L). Gas evolved and the exothermic mixture (temperature increased to 45° C.) was stirred at 75° C. for 5 h. After the reaction mixture cooled to room temperature and the catalyst settled, the majority of the solvent was decanted off through a fiberglass filter. The residue was mixed with water (6 L) and filtered. The collected solid was washed with water (1 L) and $CH_2Cl_2$ (1 L) and all the filtrates were combined. The aqueous phase was separated and extracted with $CH_2Cl_2$ (6 L), and the combined organic phases were washed with saturated aqueous $NaHCO_3$ and brine. Drying ($MgSO_4$), filtering, and concentrating afforded material that was immediately distilled (Vigreux® column, fraction boiling at 93° C., 16 mm Hg collected) to provide methyl 1-formylcyclopentanecarboxylate as a clear colorless liquid (491 g, 69% yield). $^1$H-NMR (400 MHz, $CDCl_3$) δ 9.65 (s, 1 H), 3.76 (s, 3 H), 2.19-2.04 (m, 4 H), 1.78-1.58 (m, 4 H); $^{13}$C NMR (100.6 MHz, $CDCl_3$) δ 197.0, 172.6, 64.3, 51.9, 31.0, 25.3; EI-MS exact mass calcd for: $C_8H_{13}O_3$; 157.0865; found: 157.0864. This compound has been reported previously by C. R. Davis et al., *J. Org. Chem.* 1993, 58, 6843.

EXAMPLE 3

α-Amino Nitriles 1 and 2

(i.e. methyl 1-{(R)-cyano-{1(S)-(phenylethyl) amino}methyl}cyclopentanecarboxylate and methyl 1-{(S) cyano-{1(S)-(phenylethyl)amino}methyl}- cyclopentanecarboxylate, respectively)

To a 3 L flask equipped with a mechanical stirrer and a pressure equalizing funnel was added under a nitrogen atmosphere methyl 1-formylcyclopentanecarboxylate (59.4 g, 0.378 mol), (S)-α-methylbenzylamine (47.0 g, 0.388 mol), hexane (1.3 L), and 4 Å molecular sieves (90 g). This mixture was stirred under nitrogen at room temperature for 19 h after which time it was cooled to −5° C. (ice-salt bath). $Et_2AlCl$ (24 mL, 0.19 mol) was added via a syringe followed by trimethylsilyl cyanide (56 mL, 0.42 mol) dropwise over 15 min. The reaction mixture was stirred under nitrogen at −5 to 0° C. for 3 h after which time a 1 M aqueous solution of $K_2CO_3$ (700 mL) was slowly added. The resulting slurry was filtered through diatomaceous earth, and the pad was rinsed with hexane and $Et_2O$. The organic phase was washed with brine, dried ($MgSO_4$), filtered and concentrated to afford a very pale yellow oil which eventually solidified to provide a 30:1 mixture of 2 and 1 (105 g, 96%) as a white solid. Pure 2 was readily obtained by crystallization from hexane: mp 70–73° C.; $[α]_D^{25}$ 126° (c 1.89, MeOH); $^1$H-NMR (400 MHz, $CDCl_3$) δ 7.35-7.25 (m, 5 H), 4.03 (br q, J=6.5 Hz, 1 H), 3.69 (s, 3 H), 3.32 (d, J=12.5 Hz, or br s, 1 H), 2.32-2.24 (m, 1 H), 2.01 (br d, J=12.5 Hz, 1 H), 1.97-1.92 (m, 1 H), 1.88-1.81 (m, 1 H), 1.74-1.59 (m, 4 H), 1.53-1.47 (m, 1 H), 1.36 (d, J=6.5 Hz, 3 H); $^{13}$C NMR (100.6 MHz, $CDCl_3$) δ 175.11, 143.08, 128.52, 127.68, 127.10, 119.12, 56.59, 56.49, 54.87, 52.24, 35.00, 33.08, 25.54, 25.09, 24.86; EI-MS (M-CH3) exact mass calcd for $C_{16}H_{19}N_2O_2$: 271.1447; found: 271.1461; Anal. calcd for $C_{17}H_{22}N_2O_2$: C, 71.30; H, 7.74; N, 9.78. Found: C, 71.16; H, 7.76; N, 9.73. Characteristic $^1$H NMR signals for amino nitrile 1: (400 MHz, $CDCl_3$) δ 3.91 (d, J=12.5 Hz, 1 H), 3.74 (s, 3 H), 1.31 (d, J=6.5 Hz, 3 H).

EXAMPLE 4

Equilibration of α-Amino Nitriles 1 and 2

To a solution of crude 1 and 2 (1.3:1, 37 g,~0.13 mol) (mixture will be of varying purity depending on the isolated mother liquors from the previous reaction) in MeOH (300 mL) was added $K_2CO_3$ (9 g, 65 mmol). The resultant mixture was stirred at room temperature for 5 days or until the original ratio of 1.3:1 becomes 1:~4.5 (checked by NMR). The MeOH was removed under reduced pressure and the residue partitioned between water and $CH_2Cl_2$. The organic phase was washed with water, dried ($MgSO_4$), filtered, and concentrated to provide an yellow-orange residue. This material was filtered through a pad of silica, followed by rinsing with EtOAc- hexane (1:7). The combined filtrate and washing were concentrated. The residue was crystallized from hexane (~2 times the volume of residue) to provide pure 2 (15.4 g).

EXAMPLE 5

Amino Amide 3 (i.e. methyl 1-{2-Amino-2-oxo-{1(S) -(phenylethyl)amino}methyl}cyclopentanecarboxylate To a 12 L flask equipped with a mechanical stirrer, thermometer, and a pressure equalizing funnel was added $CH_2Cl_2$ (4 L) and amino nitrile 2 (674 g, 2.35 mol). This solution was cooled below 0° C. with an ice salt bath, and concentrated sulfuric acid (650 mL) was added at a rate so that the reaction temperature remained below 10° C. The reaction mixture, which deposits an orange gum, was stirred below 5° C. for 7 h. Approximately 1.5 kg of ice were added to the reaction mixture, and 10 M aqueous NaOH (2 L or until pH reaches 12) was added at such a rate which maintained an internal temperature of less than 20° C. Vigorous stirring was required to effect efficient neutralization since three layers form. The aqueous phase was extracted with $CH_2Cl_2$ (2×800 mL) and EtOAc (400 mL) and the combined organic phases were washed with water and brine. Drying ($MgSO_4$), filtering, and concentrating afforded compound 3 as a white solid (642 g, 90%): mp 133–134° C.; $[α]_D^{25}$,36° (c 2.95, MeOH); $^1$H-NMR (400 MHz, $CDCl_3$) δ 7.33-7.25 (m, 5 H), 6.44 (br s, 1 H), 5.62 (br s, 1 H), 3.62 (q, J=6.5 Hz, 1 H), 3.61 (s, 3 H), 3.10 (s, 1 H), 2.09-2.00 (m, 3 H), 1.86-1.83 (m, 1 H), 1.66-1.49 (m, 5 H) 1.36 (d, J=6.5 Hz, 3 H); $^{13}$C NMR (100.6 MHz, $CDCl_3$) δ 176.65, 175.29, 144.52, 128.38, 127.19, 126.86, 64.48, 57.18, 56.91, 51.95, 33.41, 32.20, 24.86, 24.67, 24.58; FAB-MS exact mass calcd for $C_{17}H_{25}N_2O_3$: 305.1856; found: 305.1865; Anal. calcd for $C_{17}H_{24}N_2O_3$: C, 67.08; H, 7.95; N, 9.20. Found: C, 66.96; H, 8.02; N, 9.19.

EXAMPLE 6

(S)-α-Amino-1-carboxycyclopentaneacetic Acid (HCl salt for NMR)

To a 4 L flask equipped with inlets for hydrogen balloons and a large magnetic stirring bar was added amino amide 3 (641 g, 2.11 mol), MeOH (4.5 L), and 2 N aqueous HCl (1 L). 20% Pd(OH)$_2$ on charcoal (54.7 g) was carefully added. The flask was evacuated under aspirator pressure for 10 min, and H$_2$ gas was introduced. The reaction mixture was stirred at room temperature (20–22° C.) for 17 h, filtered through diatomaceous earth, and concentrated under reduced pressure to provide a white solid (578 g). This material was dissolved in 6 N aqueous HCl (2.6 L). The solution was heated at reflux for 21 h. Concentration under reduced pressure provided the hydrochloride salt of (S)-α-amino-1-carboxycyclopentaneacetic acid as a pale yellow solid. This material was dissolved in 600 mL of water, filtered, and the pH was adjusted to pH 4.5 with concentrated $NH_4OH$ (pH meter). The resulting white solid was collected by filtration and dried under reduced pressure (290 g, 73% yield):

mp>250° C.; [α]$_D^{25}$+30.5° (c 1.10, HOAc-H$_2$O, 1:1); $^1$H-NMR (400 MHz, DMSO-D6) δ 11.10-7.50 (br s, 2 H), 3.69 (s, 1 H), 2.07-2.02 (m, 1 H), 1.94-1.89 (m, 1 H), 1.74-1.43 (m, 6 H); $^{13}$C NMR (100.6 MHz, DMSO-D6) δ 176.20, 169.70, 57.36, 53.99, 33.24, 32.85, 25.03, 24.28; CI-MS exact mass calcd for C$_8$H$_{14}$NO$_4$: 188.0923; found: 188.0921; Anal. calcd for C$_8$H$_{13}$NO$_4$: C, 51.33; H, 7.00; N, 7.48. Found: C, 51.30; H, 7.04; N, 7.62.

EXAMPLE 7

N-Boc Derivative of (S)-α-Amino-1-carboxycyclopentaneacetic Acid

To a solution of NaOH (15.4 g, 0.385 mol) in water (75 mL) was added the title compound of example 6 (28 g, 0.15 mol). Upon dissolution, tert-butanol (75 mL) was added. The resultant solution was cooled to 0° C. Di-tert-butyl dicarbonate (49 g, 0.22 mol, warmed to effect melting) was added dropwise over 20 min. The pH of the reaction mixture was maintained around 10–11 with 5 M aqueous NaOH, and completion of the reaction was monitored by TLC and NMR. The mixture was diluted with water (100 mL) and extracted with Et$_2$O (3×150 mL). The aqueous phase was cooled to 0° C., acidified to pH 3 by the slow addition of concentrated HCl, and extracted EtOAc (3×150 mL). The combined organic extracts were washed with water and brine, dried (MgSO$_4$), filtered and concentrated to afford the N-Boc derivative, i.e.the title compound, as a white solid (42 g, 96% yield). This material was of sufficient purity to be used for subsequent reactions: mp 165–167° C.; [α]$_D^{25}$-19.8° (c 0.90, MeOH); $^1$H-NMR (400 MHz, DMSO-D6) δ 10.78 (br s, 2 H), 6.83 (q, J=10.1 Hz, 1 H), 4.54 (d, J=9.9 Hz, 1 H), 2.00-1.97 (m, 1 H), 1.82-1.52 (m, 7 H), 1.40 (s, 9 H); $^{13}$C NMR (100.6 MHz, DMSO-D6) δ 177.12, 172.31, 155.91, 78.34, 57.64, 55.04, 34.37, 31.14, 28.12, 25.27; FAB-MS exact mass calcd for C$_8$H$_{14}$NO$_4$: 288.1447; found: 288.1440; Anal. calcd for C$_8$H$_{13}$NO$_4$: C, 54.35; H, 7.37; N, 4.88. Found: C, 54.44; H, 7.60; N, 4.91.

We claim:
1. A process for preparing (S)-α-amino-1-carboxycyclopentaneacetic acid which comprises the following steps:

(i) reacting methyl 1-formylcyclopentanecarboxylate with the chiral amine auxiliary (S)-α-methylbenzylamine to obtain the corresponding Schiff base, (ii) reacting the Schiff base with a cyanide source in the presence of a Lewis acid to obtain a mixture of the α-amino nitriles of formulae 1 and 2

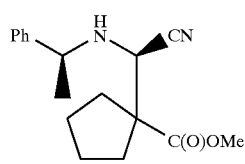

(1)

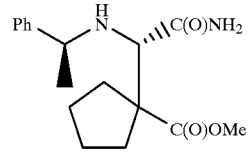

(2)

in a R:S ratio of at least 1:15-30, (iii) subjecting the latter mixture to selective acid hydrolysis to obtain predominantly the amino amide 3

(3)

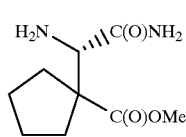

(iv) subjecting the amino amide 3 to hydrogenolysis in the presence of aqueous HCl to obtain the corresponding N-terminal derivative 4

(4)

followed by hydrolysis of the latter compound with excess 6 N aqueous HCl to obtain the hydrochloride salt of (S)-α-amino-1-carboxycyclopentaneacetic acid; and (v) reacting the hydrochloride salt with a base capable of transforming the hydrochloride salt to (S)-α-amino-1-carboxycyclopentaneacetic acid.

2. The process of claim 1 wherein the mixture of the α-amino nitriles of formulae 1 and 2, obtained according to step (ii), is crystalized from or triturated in hexane to give essentially, enantiomerically pure α-amino nitrile 2, which in turn is subjected serially to steps iii, iv and v to give (S)-α-amino-1-carboxycyclopentaneacetic acid.

3. The process of claim 1 wherein the cyanide source is selected from the group consisting of trimethylsilyl cyanide, acetone cyanohydrin, diethylaluminum cyanide and potassium cyanide, and the Lewis acid is selected from the group consisting of TiCl$_4$, SnCl$_4$, ZnCl$_2$, trimethylsilyl trifluoromethanesulfonate, Me$_3$Al, Et$_2$AlCl and EtAlCl$_2$.

4. The process of claim 2 wherein the cyanide source is selected from the group consisting of trimethylsilyl cyanide, acetone cyanohydrin, diethylaluminum cyanide and potassium cyanide, and the Lewis acid is selected from the group consisting of TiCl$_4$, SnCl$_4$, ZnCl$_2$, trimethylsilyl trifluoromethanesulfonate, Me$_3$Al, Et$_2$AlCl and EtAlCl$_2$.

5. The process of claim 2 wherein the cyanide source is trimethylsilyl cyanide and the Lewis acid is EtAlCl$_2$.

6. An amino amide of formula 3 of claim 1.

7. An N-terminal derivative of formula 4 of claim 1.

* * * * *